United States Patent [19]

Merger et al.

[11] Patent Number: 5,239,120
[45] Date of Patent: * Aug. 24, 1993

[54] PREPARATION OF 2-(3-AMINOPROPYL)-CYCLOALKYLAMINES

[75] Inventors: Franz Merger, Frankenthal; Claus-Ulrich Priester, Ludwigshafen; Gerhard Koppenhoefer, Roemerberg; Wolfgang Harder, Weinheim; Tom Witzel; Helmut Lermer, both of Ludwigshafen; Ulrich Koehler, Heidelberg, all of Fed. Rep. of Germany

[73] Assignee: BASF Aktiengesellschaft, Ludwigshafen, Fed. Rep. of Germany

[ * ] Notice: The portion of the term of this patent subsequent to Nov. 24, 2009 has been disclaimed.

[21] Appl. No.: 676,087

[22] Filed: Mar. 27, 1991

[30] Foreign Application Priority Data

Mar. 30, 1990 [DE] Fed. Rep. of Germany ....... 4010254

[51] Int. Cl.$^5$ ............................................ C07C 211/35
[52] U.S. Cl. ..................... 564/454; 564/453; 564/446; 564/448; 564/473; 564/490; 564/461
[58] Field of Search ............... 564/453, 446, 461, 490, 564/448, 454, 473, 454

[56] References Cited

U.S. PATENT DOCUMENTS

| 3,143,570 | 8/1964 | Caldwell et al. | 564/448 |
| 4,042,629 | 8/1977 | Kershaw | 564/490 |
| 4,429,157 | 1/1984 | Disteldorf et al. | 564/446 |

FOREIGN PATENT DOCUMENTS

| 42119 | 12/1981 | European Pat. Off. . |
| 242119 | 12/1981 | European Pat. Off. . |
| 3011656 | 10/1981 | Fed. Rep. of Germany . |
| 55-19896 | 7/1970 | Japan . |
| 1252427 | 11/1971 | United Kingdom . |
| 1498998 | 1/1978 | United Kingdom . |

OTHER PUBLICATIONS

Chemical Abstracts, vol. 73, No. 17, Oct. 26, 1970, 87521z.

Primary Examiner—Richard L. Raymond
Assistant Examiner—Shailendra Kumar
Attorney, Agent, or Firm—John H. Shurtleff

[57] ABSTRACT

A process for the preparation of a 2-(3-aminopropyl)-cycloalkylamine of the general formula I

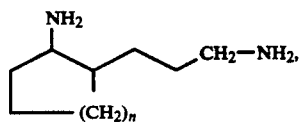

in which the subscript n is an integer from 1 to 4, from a 2-(2-cyanoethyl)-cycloalkanone of the general formula II

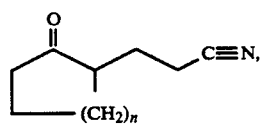

in which the subscript n has the meaning stated, wherein the following stages are carried out in discrete reaction chambers:

a) the 2-(2-cyanoethyl)-cycloalkanone of formula II is reacted in a first reaction chamber with excess ammonia over an acidic heterogeneous catalyst at a temperature from 20° to 150° C. and a pressure of from 15 to 500 bar, and b) in a second reaction chamber, the reaction product from stage a) is hydrogenated at a temperature of from 60° to 150° C. and a pressure of from 50 to 300 bar in the presence of excess ammonia over a catalyst containing cobalt, nickel, ruthenium, and/or some other noble metal, which catalyst optionally contains a basic component or is supported on neutral or basic supporting material.

20 Claims, No Drawings

PREPARATION OF 2-(3-AMINOPROPYL)-CYCLOALKYLAMINES

The present invention relates to a novel process for the preparation of a 2-(3-aminopropyl)-cycloalkylamine from a 2-(2-cyanoethyl)-cycloalkanone.

JP 70/19,896 describes a process for the preparation of 2-(3-aminopropyl)-cyclohexylamine, in which 2-(2-cyanoethyl)-cycloethyl)-cyclohexanone is reacted with ammonia and hydrogen in the presence of a hydrogenation catalyst. In this batch process, a solution of 2-(2-cyanoethyl)-cyclohexanone in methanol is hydrogenated i the presence of 10% w/w of Raney nickel and 14 moles of ammonia at 130° C. and 110 bar to produce 2-(3-aminopropyl)-cyclohexylanine after a reaction time of 5 hours. Catalysts proposed for said process are Raney nickel, Raney cobalt, catalysts based on nickel, cobalt or copper, and noble metal catalysts (platinum, palladium, rhodium, and ruthenium) for use at a reaction temperature ranging from 100° to 150° C. This process suffers from the drawback that the reaction time is very long and thus the space-time yield is inadequate for industrial utilization of the process. Furthermore, the product yield of this process is unsatisfactory (cf. Comparative Example 1 below).

EP-A 42,119 describes a process for the preparation of primary mono- and di-amines by reacting oxo compounds, which may or may not contain other reducible groups, with ammonia and hydrogen in the presence of conventional hydrogenation catalysts, before which reaction the said oxo compounds are caused to enter into a preliminary reaction with ammonia at a temperature of from 10° to 200° C. and a pressure of from 1 to 300 bar in the presence of organic or inorganic ion exchanges in the ammonium form and serving as imine-forming catalysts. The Examples of this citation show that the process applies exclusively to the aminating hydrogenation of 3-cyano-3,5,5-trimethyl-cyclohexanone (isophoronenitrile) and 2,2,6,6-tetramethyl-4-piperidone (triacetonamine). When isophoronenitrile is subjected to such aminating hydrogenation, the use of the organic ion exchanger Lewatit SP ® 120 in the imination leads to a slight yield improvement over non-use of the catalyst (cf. Comparative Example 3 in EP-A 42,119: yield=90.3%. whereas yield with Lewatit SP ® 120=93.9 to 94.7%).

It is thus an object of the present invention to provide a process for the preparation of a 2-(3-aminopropyl)-cycloalkylamine from a 2-(2-cyanoethyl)-cycloalkanone under industrially feasible conditions, which provides industrially acceptable yields and space-time yields.

Accordingly, we have fond a novel, improved process for the preparation of a 2-(3-aminopropyl)-cycloalkylamine of the general formula I

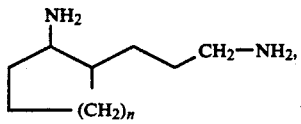

in which the subscript n is an integer from 1 to 4, from a 2-(2-cyanoethyl)-cycloalkanone of the general formula II

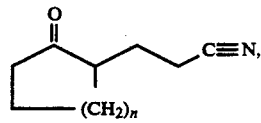

in which the transcript n has the meaning stated, wherein the following stages are carried out in discrete reaction chambers:

a) the 2-(2-cyanoethyl)-cycloalkanone of formula II is reacted in a first reaction chamber with excess ammonia over an acidic heterogeneous catalyst at a temperature of from 20° to 150° C. and a pressure of from 15 to 500 bar, and b) in a second reaction chamber, the reaction product from stage a) is hydrogenated at a temperature of from 60° to 150° C. and a pressure of from 50 to 500 bar in the presence of excess ammonia over a catalyst containing cobalt, nickel, ruthenium, and/or some other noble metal, which catalyst optionally contains a basic component or is supported by neutral or basic supporting material.

We have also found the novel compound 2-(3-aminopropyl)-cyclopentylamine.

The process of the invention can be carried out as follows using two discrete reaction chambers:

a) in a first stage, a 2-(2-cyanoethyl)-cycloalkanone is reacted with excess ammonia at a temperature of from 20° to 150° C., preferably from 30° to 130° C. and more preferably from 50° to 100° C. and under a pressure of from 15 to 500 bar, preferably from 100 to 350 bar to yield the 2-(2-cyanoethyl)-cycloalkylimine.

Suitable acidic heterogeneous catalysts are metal compounds having the character of a Lewis acid or Bronsted acid, eg aluminum oxide, silicon oxide, titanium dioxide, zirconium dioxide, and also phosphates, eg aluminum phosphate, or silicates, eg amorphous or crystalline aluminosilicates. We prefer to use aluminum oxide, titanium dioxide, zirconium oxide and silicon dioxide, particularly aluminum oxide and titanium dioxide. If desired, the acidity of the catalyst can be raised by doping it with a halide. Thus halide-doped catalysts may be used such as chloride on aluminum oxide or chloride on titanium dioxide.

For the imination a throughput of from 0.01 to 10 kg, preferably from 0.02 to 5 kg and more preferably from 0.05 to 3 kg, of 2-(2-cyanoethyl)-cycloalkanone per kg of catalyst per hour is maintained. The amount of $NH_3$ used per mole of 2-(2-cyanoethyl)-cycloalkanone during the imination is conveniently but not obligatorily from 5 to 500 moles, preferably from 30 to 400 moles and more preferably from 50 to 300 moles. The imination may also be carried out in the presence of a solvent such as an alkanol or tetrahydrofuran.

The imination is preferably carried out continuously in a pressure vessel or cascade of pressure vessels. In a preferred embodiment, the 2-(2-cyanoethyl)-cycloalkanone and $NH_3$ are passed through a tubular reactor containing the imination catalyst in the form of a fixed bed.

The overall residence time in stage a) is determined by the throughput rate and the amount of ammonia used. It is advantageously in the range of 0.5 to 120 minutes, preferably 1 to 40 minutes and more preferably 1.5 to 20 minutes.

b) The resulting product is passed to a second stage where it is subjected to catalytic hydrogenation involving from 3 to 10,000, preferably 4.5 to 30, mole equivalents of hydrogen, if necessary after the addition of a further amount of ammonia.

For the catalytic hydrogenation, the temperature is kept at a value of from 60° to 150° C., preferably from 70° to 140° C. and more preferably from 80° to 130° C. and the pressure at a value between 50 and 500 bar, preferably between 100 and 350 bar and more preferably between 150 and 300 bar.

The throughput rate is advantageously in the range of 0.01 to 5 kg/kg/h, preferably 0.02 to 2.5 kg/kg/h and more preferably 0.05 to 2 kg/kg/h.

The hydrogenation is advantageously carried out in liquid ammonia. The amount of ammonia used per mole of 2-(2-cyanoethyl)-cycloalkylimine is preferably from 5 to 500 moles, more preferably from 30 to 400 moles and most preferably from 50 to 300 moles. It is convenient to select the same ammonia rate as is used in the preceding synthesis of 2-(2-cyanoethyl)-cycloalkylimine from the corresponding 2-(2-cyanoethyl)-cycloalkanone. Alternatively, the desired ammonia rate may be achieved by adding fresh ammonia to the ammonia stream prior to hydrogenation.

The aminating hydrogenation of the 2-(2-cyanoethyl)-cycloalkylimine is preferably carried out continuously, for example in a pressure-tight stirred vessel or a cascade of such vessels. In a particularly preferred embodiment, a tubular reactor is used in which the mixture of products leaving the imination of the 2-(2-cyanoethyl)-cycloalkanone is passed through a fixed catalyst bed acting either as a bubble bed or as a trickle bed.

The stages a) and b) may alternatively be carried out in a single reactor in which case the imination is conveniently carried out in the presence of hydrogen.

For continuous operation in a tubular reactor without recycling, the overall residence time is determined by the throughput rate and the amount of ammonia used. It ranges from 0.5 to 120 minutes, preferably from 1 to 40 minutes and more preferably from 1.5 to 20 minutes.

Following the hydrogenation, the excess ammonia is separated off, if necessary under pressure. The resulting 2-(3-aminopropyl)-cycloalkylamine can be isolated by fractional distillation. Piperidines (eg decahydroquinoline from 2-(2-cyanoethyl)-cyclohexanone or 2-azabicyclo[4.3.0]nonane from 2-(2-cyanoethyl)-cyclopentanone) occur as by-products but only to a minor extent.

In principle, all commonly used hydrogenation catalysts can be employed in the hydrogenation stage, for example catalysts containing nickel, cobalt, iron, copper, ruthenium, or any other noble metal in group VIII of the periodic table. We prefer to use ruthenium, cobalt or nickel catalysts, ruthenium and cobalt catalysts being particularly preferred. The catalytically active metals may be in the form of solid catalysts or supported catalysts. Examples of suitable supports are aluminum oxide, titanium dioxide, zirconium dioxide, zinc oxide, and magnesium oxide/aluminum oxide, and hydrogenation catalysts are preferred which contain basic components such as oxides and hydroxides of alkali metals and alkaline earth meals. Basic supports are therefore particularly preferred, eg β-aluminum oxide or magnesium oxide/aluminum oxide, especially magnesium oxide/aluminum oxide in which the content of magnesium oxide is from 5 to 40%. The support containing magnesium oxide and aluminum oxide may be amorphous or a spinel.

We particularly prefer to use cobalt or ruthenium with a content of basic components as hydrogenation catalyst. Such catalysts are produced industrially by conventional methods. For example, ruthenium on a basic support is obtained by depositing an aqueous ruthenium salt solution, eg ruthenium chloride or ruthenium nitrate, on to the appropriate support. The concentration of the ruthenium on the support ranges from 0.1 to 10%, preferably from 0.5 to 5% and more preferably from 1 to 4%. After drying and, possibly, after calcination at a temperature of from 120° to 500° C. and preferably from 200° to 400° C., the ruthenium catalyst is activated in a stream of hydrogen at a temperature of from 180° to 250° C. and preferably from 190° to 230° C. and under a pressure of from 1 to 500 bar, preferably from 20 to 300 bar, for a period of from 1 to 20 hours, preferably 2 to 10 hours.

The said ruthenium catalysts may optionally contain other metals, such as palladium or iron. The iron content is generally between 0.5 and 5% and the palladium content between 0.1 and 5%.

The ruthenium catalysts are characterized by the fact that they permit particularly high throughput rates and thus provide particularly high space-time yields.

The basic cobalt catalysts contain at least one basic component such as $Li_2O$, $Na_2O$, $K_2O$, MgO, CaO, SrO, or BaO. Besides this component, such catalysts contain at least one of the elements iron, nickel, manganese, chromium, molybdenum, tungsten, and phosphorus. Of particular interest are catalysts which contain, besides cobalt and a basic component, at least one of the metals iron, nickel, and manganese. The metals may be used in metallic form or in the form of their oxides. For all practical purposes, phosphorus is present in the form of phosphoric acid.

EXAMPLES

Example 1

A vertical tubular reactor (diameter 16 mm, packing height 22 cm, oil-heated double jacket) was packed with 29.9 g (43 ml) of a catalyst containing 1.8% of ruthenium on aluminum oxide (Purel SB) in the form of 1.5 mm extrudates (prepared by filling the pores of Pural SB with an aqueous ruthenium chloride solution and drying at 120° C.). Reduction of the catalyst was effected by keeping it at a temperature of 200° C. for 7 hours under a stream of 40 standard liters of hydrogen per hour at a pressure of 60 bar after the temperature had been progressively raised from 150° to 220° C. over 2 hours.

At a pressure of 200 bar and a temperature of 100° C., 9.3 ml of 2-(2-cyanoethyl)-cyclohexanone (purity 98.2%, 9.1 g, 0.060 mole) and 430 ml of liquid ammonia (258 g, 15.2 moles) were pumped per hour, through a packed tubular reactor having a capacity of 20 ml and installed upstream of the above hydrogenation reactor, the packing consisting of 12.3 g of an aluminum oxide (0.2 to 1 mm grit) doped with 1.1% of chloride, after which the said reaction mixture was passed upwardly through the hydrogenation reactor, at a pressure of 200 bar and a temperature of 90° C., together with 60 standard liters (2.7 moles) of hydrogen per hour. Gas-chromatographic analysis revealed that the product mixture contained 61.8% of 2-(3-aminopropyl)-cyclohexylamine, 33.0% of decahydroquinoline, 0.1% of octahydroquinoline and 2.3% of 2-(3-aminopropyl)- cyclohexanol, corresponding to a yield of 2-(3-aminopropyl)-cyclohexylamine of 60.4% of theory.

Example 2

A vertical tubular reactor (diameter 16 mm, packing height 50 cm, oil-heated double jacket) was packed with 173.9 g (95 ml) of a cobalt catalyst containing 5% of $Mn_2O_3$ in the form of 1 mm to 1.5 mm grit. Reduction of the catalyst was carried out at 100 bar under a stream of 150 standard liters of hydrogen per hour while the temperature was progressively raised from 100° C. to 320° C. over 46 hours and then held at 320° C. for 48 hours.

Through a tubular reactor (diameter 16 mm, packing height 50 cm, oil-heated double jacket), installed upstream of the hydrogenation reactor and packed with 41.6 g (92 ml) of a zeolite type Y which had been extruded with Aerosil 200 (ratio Y-type zeolite to Aerosil 200 9:1, ratio $SiO_2$ to $Al_2O_3$ 6:1), there were passed upwardly, per hour, 36.7 g of 2-(2-cyanoethyl)-cyclohexanone (purity 96%, 0.233 mole) and 1.475 ml of liquid ammonia (885 g, 52.1 moles) at a pressure of 250 bar and a temperature of 70° C. Hydrogen was then added to the stream at a rate of 150 standard liters (6.7 moles) per hour, and the effluent from this in-line imination reactor was passed upwardly through the hydrogenation reactor at a pressure of 250 bar and a temperature of 120° C. The product mixture was depressurized to standard pressure and fed to the top of a column (length 46 cm, diameter 3 cm) held at 40° C. and packed with 5 mm wire mesh rings in which the ammonia was removed. After an on-stream time of 19.9 hours distillation of the product had yielded, besides 189.7 g of decahydroquinoline, 431.2 g of 2-(3-aminopropyl)-cyclohexylamine, this corresponding to a yield of 2-(3-aminopropyl)-cyclohexylamine of 59.6% of theory.

Example 3

A vertical tubular reactor (diameter 16 mm, packing height 50 cm, oil-heated double jacket) was packed with 105.3 g (81 ml) of a catalyst containing 85% of CoO, 10% of CaO, and 5% of $Mn_2O_3$ in the form of 1 mm to 1.5 mm grit. Reduction of the catalyst was carried out at 100 bar under a stream of 150 standard liters of hydrogen per hour while the temperature was progressively raised from 100° C. to 330° C. over 23 hours and then held at 330° C. for 30 hours.

Through a tubular reactor (diameter 16 mm, packing height 50 cm, oil-heated double jacket), installed upstream of the hydrogenation reactor and packed with 64.4 g (92 ml) of γ-aluminum oxide there were passed upwardly, per hour, 55.4 g of 2-(2-cyanoethyl)-cyclohexanone (purity 96%, 0.352 mole) and 875 ml of liquid ammonia (525 g, 30.9 moles) at a pressure of 250 bar and a temperature of 70° C. Hydrogen was then added to the stream at a rate of 200 standard liters (8.9 moles) per hour, and the effluent from the in-line imination reactor was passed upwardly through the hydrogenation reactor at a pressure of 250 bar and a temperature of 120° C. After an on-stream of 3.5 hours the separation and distillation measures as per Example 2 had yielded, besides 33.1 g of decahydroquinoline, 138.8 of 2-(3-aminopropyl)-cyclohexylamine, this corresponding to a yield of 2-(3-aminopropyl)-cyclohexylamine of 71.5% of theory.

Example 4

Example 3 was repeated except that 29.7 g of 2-(2-cyanoethyl)-cyclohexanone (purity 96%, 0.189 mole) and 1,200 ml of liquid ammonia (720 g, 42.4 moles) were passed upwardly through the first reactor, per hour, at a pressure of 250 bar and a temperature of 70° C. Hydrogen was then added to the stream at a rate of 125 standard liters (5.6 moles) per hour, and the effluent from the in-line imination reactor was passed upwardly through the hydrogenation reactor at a pressure of 250 bar and a temperature of 125° C. After an on-stream time of 17.8 hours the separation and distillation measures as per Example 2 had yielded, besides 66.4 g of decahydroquinoline, 365 g of 2-(3-aminopropyl)-cyclohexylamine. The yield of 2-(3-aminopropyl)-cyclohexylamine was 69.7% of theory.

Example 5

A vertical tubular reactor (diameter 16 mm, packing height 50 cm, oil-heated double jacket) was packed with 176.7 g (100 ml) of a basic solid cobalt catalyst (comprising CoO containing 5% of $Mn_2O_3$ and 1.4% of $Na_2$) in the form of 1 mm to 1.5 mm grit. Reduction of the catalyst was carried out at 100 bar under a stream of 150 standard liters of hydrogen per hour while the temperature was progressively raised from 100° C. to 330° C. over 23 hours and then held at 330° C. for 30 hours.

Through a tubular reactor (diameter 16 mm, packing height 50 cm, oil-heated double jacket), installed upstream of the hydrogenation reactor and packed with 70.0 g (100 g) of γ-aluminum oxide in he form of 1.5 mm extrudates, there were passed upwardly, per hour, 10.7 g of 2-(2-cyanoethyl)-cyclohexanone (purity 97.5%, 0.069 mole) and 500 ml of liquid ammonia (300 g, 17.6 moles) at a pressure of 250 bar and a temperature of 80° C. Hydrogen was then added to the stream at a rate of 60 standard liters (2.7 moles) per hour, and the effluent from the in-line imination reactor was passed upwardly through the hydrogenation reactor at a pressure of 250 bar and a temperature of 130° C. Gas-chromatographic analysis of the hydrogenation product gave 86.3% of 2-(3-aminopropyl)-cyclohexylamine and 7.9% of decahydroquinoline, corresponding to a yield of 2-(3-aminopropyl)-cyclohexylamine of 87.1% of theory.

Example 6

A vertical tubular reactor (diameter 16 mm, packing height 50 cm, oil-heated double jacket) was packed with 176.7 g (100 ml) of a basic solid cobalt catalyst (comprising CoO containing 5% of $Mn_2O_3$ and 1.4% of $Na_2O$) in the form of 1 mm to 1.5 mm grit. Reduction of the catalyst was carried out at 100 bar under a stream of 150 standard lines of hydrogen per hour while the temperature was progressively raised from 100° C. to 330° C. over 23 hours and then held at 330° C. for 30 hours.

Through a tubular reactor (diameter 16 mm, packing height 50 cm, oil-heated double jacket), installed upstream of the hydrogenation reactor and packed with 63.5 g (100 ml) of titanium dioxide (anatase) in the form of 1.5 mm extrudates, there were passed upwardly, per hour, 16.0 g of 2-(2-cyanoethyl)-cyclohexanone (purity 97.5%, 0.103 mole) and 51 g of liquid ammonia (87 ml, 3.0 moles) at a pressure of 250 bar and a temperature of 80° C. Hydrogen was then added to the stream at ar ate of 60 standard liters per hour, and the effluent from the in-line imination reactor was passed upwardly through the hydrogenation reactor at a pressure of 250 bar and a temperature of 130° C. The effluent was depressurized to standard pressure, and the ammonia was distilled off. Gas-chromatographic analysis of the hydrogenation product gave 92.5% of 2-(3-aminopropyl)-cyclohexylamine and 4.5% of decahydroquinoline. The effluent was collected over a period of 46 hours and fractionated by distillation in a 30 cm packed column containing 3 mm glass rings. There were obtained 674 g of 2-(3-aminopropyl)-cyclohexylamine, corresponding to a yield of 91.0% of theory.

EXAMPLE 7

A vertical tubular reactor (diameter 16 mm, packing height 31 cm, oil-heated double jacket) was packed with 38.3 g (62 ml) of a catalyst containing 2.6% of ruthenium on a magnesium oxide/aluminum oxide support (ratio MgO to $Al_2O_3$ 10:90) in the form of 1 mm to 1.5 mm grit (prepared by filling the pores of a $MgO/Al_2O_3$ support with an aqueous ruthenium nitrate solution and drying at 120° C.). Reduction of the catalyst was effected by keeping it at a temperature of 220° C. for 7 hours under a stream of 50 standard liters of hydrogen per hour under standard pressure after the temperature had been progressively raised from 100° to 220° C. over 6 hours.

At a pressure of 270 bar and a temperature of 100° C., 11.9 ml of 2-(2-cyanoethyl)-cyclohexanone (purity 98.2%, 11.7 g, 0.077 mole) and 430 ml of liquid ammonia (258 g, 15.2 moles) were pumped, per hour, through a packed tubular reactor having a capacity of 20 ml and installed upstream of the hydrogenation reactor, the packing consisting of 10.3 g of a zeolite type Y (zeolite type Y containing 0.14% of Na, ratio $SiO_2$ to $Al_2O_3$ 5.8:1) in the form of 1 mm to 1.25 mm grit, after which the said reaction mixture was passed upwardly through the hydrogenation reactor, at a pressure of 200 bar and a temperature of 90° C., together with 60 standard liters (2.7 moles) of hydrogen per hour. Gas-chromatographic analysis revealed that the product mixture contained 84.1% of 2-(3-aminopropyl)-cyclohexylamine, 11.4% of decahydroquinoline, and 0.5% of 2-(3-aminopropyl)-cyclohexanol, corresponding to a yield of 2-(3-aminopropyl)-cyclohexylamine of 84.4% of theory.

Example 8

A vertical tubular reactor (diameter 16 mm, packing height 15 cm, oil-heated double jacket) was packed with 24.8 g (30.2 ml) of a catalyst containing 2.2% of ruthenium on a magnesium oxide/aluminum oxide support (10:90) in the form of 1 mm to 1.5 mm grit (prepared by filling the pores of a magnesium oxide/aluminum oxide support with an aqueous ruthenium nitrate solution and drying at 120° C.). Reduction of the catalyst was effected by keeping it at a temperature of 220° C. for 7 hours under a stream of 60 standard liters of hydrogen per hour under standard pressure after the temperature had been progressively raised from 100° to 220° C. over 6 hours.

At a pressure of 220 bar and a temperature of 100° C., 9.2 ml of 2-(2-cyanoethyl)-cyclohexanone (purity 98.2%, 9.0 g, 0.060 mole) and 270 ml of liquid ammonia (162 g, 9.5 moles) were pumped, per hour, through a packed tubular reactor having a capacity of 60 ml and installed upstream of the hydrogenation reactor, the packing consisting of 38.1 g of titanium dioxide (anatase) in the form of 1.5 mm extrudates, after which the said reaction mixture was passed downwardly through the hydrogenation reactor, at a pressure of 202 bar and a temperature of 90° C., together with 30 standard liters (1.3 moles) of hydrogen per hour. The product mixture was depressurized to standard pressure and fed to the top of a column (length 20 cm) held at 40° C. and packed with a 8 mm glass rings, through which 40 l/h of nitrogen were blown countercurrently. The bottoms consisted of 32.7 g/h of stripped product mixture. Gas-chromatographic analysis revealed that this product mixture contained 83.0% of 2-(3-aminopropyl)-cyclohexylamine, 12.6% of decahydroquinoline, 1.1% of octahydroquinoline, and 0.6% of 2-(3-aminopropyl)-cyclohexanol. The yield of 2-(3-aminopropyl)-cyclohexylamine was 83.1% of theory.

Example 9

Example 8 was repeated except that the hydrogen rate through the hydrogenation reactor was 60 l/h (2.7 moles/h) instead of 30 l/h (STP). The product mixture was worked up as described in Example 7. Gas-chromatographic analysis revealed that the product mixture contained 78.4% of 2-(3-aminopropyl)-cyclohexylanine, 17.8% of decahydroquinoline, 0.3% of octahydroquinoline, and 1.5% of 2-(3-aminopropyl)-cyclohexanol. The yield of 2-(3-aminopropyl)-cyclohexylamine was 78.1% of theory.

Example 10

Example 8 was repeated except that 8.7 ml of 2-(2-cyanoethyl)-cyclohexanone (purity 98.2%, kF8.5 g, 0.056 mole) and 600 ml of liquid ammonia (360 g, 21.2 moles) were pumped, per hour, through the imination reactor at a pressure of 219 bar and a temperature of 100° C., after which the said reaction mixture was passed downwardly through the hydrogenation reactor, at a pressure of 203 bar and a temperature of 120° C., together with 60 standard liters (2.7 moles) of hydrogen per hour. Gas-chromatographic analysis revealed that the product mixture contained 83.0% of 2-(3-aminopropyl)-cyclohexylamine, 14.8% of decahydroquinoline, and 0.1% of 2-(3-aminopropyl)-cyclohexanol, corresponding to a yield of 2-(3-aminopropyl)-cyclohexylamine of 83% of theory.

Example 11

Example 8 was repeated except that 18.4 ml of 2-(2-cyanoethyl)-cyclohexanone (purity 98.2%, 18 g, 0.119 mole) and 400 ml of liquid ammonia (240 g, 14.1 moles) were pumped, per hour, through the imination reactor at a pressure of 212 bar and a temperature of 100° C., after which the said reaction mixture was passed downwardly through the hydrogenation reactor, at a pressure of 204 bar and a temperature of 120° C., together with 60 standard liters (2.7 moles) of hydrogen per hour. Gas-chromatographic analysis revealed that the product mixture contained 75.7% of 2-(3-aminopropyl)-cyclohexylanine, 21.6% of decahydroquinoline, and 0.6% of 2-(3-aminopropyl)-cyclohexanol, corresponding to a yield of 2-(3-aminopropyl)-cyclohexylamine of 75.1% of theory.

Example 12

Example 8 was repeated except that 28.8 ml of 2-(2-cyanoethyl)-cyclohexanone (purity 98.2%, 28.2 g, 0.187 mole) and 460 ml of liquid ammonia (276 g, 16.2 moles) were pumped, per hour, through the imination reactor at a pressure of 220 bar and a temperature of 100° C., after which the said reaction mixture was passed downwardly through the hydrogenation reactor, at a pressure of 203 bar and a temperature of 120° C., together with 60 standard liters (2.7 moles) of hydrogen per hour. Gas-chromatographic analysis revealed that the product mixture contained 74.1% of 2-(3-aminopropyl)-cyclohexylamine, F22.3% of decahydroquinoline, and 1.1% of 2-(3-aminopropyl)-cyclohexanol, corresponding to a yield of 2-(3-aminopropyl)-cyclohexylamine of 73.4% of theory.

Example 13

Example 8 was repeated except that 29.1 ml of 2-(2-cyanoethyl)-cyclohexanone (purity 98.2%, 28.5 g, 0.188 mole) and 460 ml of liquid ammonia (276 g, 16.2 moles) were pumped, per hour, through the imination reactor at a pressure of 220 bar and a temperature of 100° C., after which the said reaction mixture was passed downwardly through the hydrogenation reactor, at a pressure of 200 bar and a temperature of 120° C., together with 60 standard liters (2.7 moles) of hydrogen per hour. The product mixture was depressurized to standard pressure and fed to the top of a column (length 20 cm) held at 40° C. and packed with 8 mm glass rings, through which 40 l/h of nitrogen were blown countercurrently. The bottom consisted of 32.7 g/h of stripped product mixture. Gas-chromatographic analysis revealed that this product mixture contained 70.7% of 2-(3-aminopropyl)-cyclohexylamine, 25.5% of decahydroquinoline, 0.2% of octahydroquinoline, and 1% of 2-(3-aminopropyl)-cyclohexanol. After an on-stream time of 5.6 hours the product mixture (183 g) was separated by fractional distillation. There were obtained, besides 3.4 g of residues and 34.4 g of decahydroquinoline (b.p.=60° to 73° C./10 mm Hg), 112.8 g of 2-(3-aminopropyl)-cyclohexylamine (b.p.=87° to 90° C./0.5 mm Hg), corresponding to a yield of 2-(3-aminopropyl)-cyclohexylamine of 68.1% of theory.

Example 14

Example 8 was repeated except that 53.2 ml of 2-(2-cyanoethyl)-cyclohexanone (purity 98.2%, 52.1 g, 0.348 mole) and 600 ml of liquid ammonia (360 g, 21.2 moles) were pumped, per hour, through the imination reactor at a pressure of 221 bar and a temperature of 100° C., after which the said reaction mixture was passed downwardly through the hydrogenation reactor, at a pressure of 203 bar and a temperature of 120° C., together with 120 standard liters (5.4 moles) of hydrogen per hour. Gas-chromatographic analysis revealed that the product mixture contained 66.2% of 2-(3-aminopropyl)-cyclohexylamine, 28.2% of decahydroquinoline, 1.7% of octahydroquinoline, and 1.3% of 2-(3-aminopropyl)-cyclohexanol, corresponding to a yield of 2-(3-aminopropyl)-cyclohexylamine of 65.0% of theory.

Example 15

A vertical tubular reactor (diameter 16 mm, packing height 24 cm, oil-heated double jacket) was packed with 40.4 g (47 ml) of a catalyst containing 2.7% of ruthenium on a magnesium oxide/aluminum oxide support (ratio MgO to $Al_2O_3$=10:90) in the form of 1 mm to 1.5 mm grit (prepared by filling the pores of an MgO/$Al_2O_3$ support with an aqueous ruthenium chloride solution and drying at 120° C.). Reduction of the catalyst was effected by keeping it at a temperature of 220° C. for 7 hours under a stream of 50 standard liters of hydrogen per hour under standard pressure after the temperature had been progressively raised from 100° to 220° C. over a period of 6 hours.

Through a tubular reactor having a capacity of 20 ml, installed up-stream of the hydrogenation reactor and packed with 11.4 g of a zeolite type Y which had been extruded with Aerosil 200 (Y-type zeolite containing 0.22% of Na, ratio Y-type zeolite to Aerosil 200 90:10, ratio $SiO_2$ to $Al_2O_3$6:1) in the form of 1 mm to 1.25 mm grit, there were passed, per hour, 11.4 ml of 2-(2-cyanoethyl)-cyclohexanone (purity 98.2%, 11.1 g, 0.074 mole) and 430 ml of liquid ammonia (258 g, 15.2 moles) at a pressure of 310 bar and a temperature of 100° C., after which the mixture was passed downwardly through the hydrogenation reactor, at a pressure of 300 bar and a temperature of 90° C., together with a stream of 60 l/h (STP) (2.7 moles/h) of hydrogen. Gas-chromatographic analysis revealed that the product mixture contained 73.6% of 2-(3-aminopropyl)-cyclohexylamine, 24.2% of decahydroquinoline, and 0.3% of 2-(3-aminopropyl)-cyclohexanol, corresponding to a yield of 2(3-aminopropyl)-cyclohexylamine of 72.8% of theory.

Example 16

A vertical tubular reactor (diameter 16 mm, packing height 30 cm, oil-heated double jacket) was packed with 38.9 g (60 ml) of a catalyst containing 5.4% of ruthenium and 0.8% of iron on a magnesium oxide/aluminum oxide support (ratio MgO to $Al_2O_3$=10:90) in the form of 1 mm to 1.5 mm grit (prepared by filling the pores of an MgO/$Al_2O_3$ support with an aqueous iron nitrate/ruthenium nitrate solution and drying at 120° C.). Reduction of the catalyst was effected by keeping it at a temperature of 220° C. for 7 hours under a stream of 50 standard liters of hydrogen per hour under standard pressure after the temperature had been progressively raised from 100° C. over a period of 6 hours.

Through a tubular reactor having a capacity of 60 ml, installed up-stream of the hydrogenation reactor and packed with 38.1 g of titanium dioxide (anatase) in the form of 1.5 mm extrudates, there were pumped, per hour, 24.2 ml of 2-(2-cyanoethyl)-cyclohexanone (purity 98.2%, 23.7 g, 0.157 mole) and 430 ml of liquid ammonia (258 g, 15.2 moles) at a pressure of 280 bar and a temperature of 80° C., after which the mixture was passed upwardly through the hydrogenation reactor at a pressure of 200 bar and a temperature of 90° C. together with a stream of 60 l/h (STP) (2.7 moles/h) of hydrogen. Gas-chromatographic analysis revealed that the product mixture contained 76.4% of 2-(3-aminopropyl)-cyclohexylamine, 18.2% of decahydroquinoline, 0.4% of octahydroquinoline, and 0.9% of 2-(3-aminopropyl)-cyclohexanol, corresponding to a yield of 2-(3-aminopropyl)-cyclohexylamine of 76% of theory.

Example 17

A vertical tubular reactor (diameter 16 mm, packing height 15 cm, oil-heated double jacket) was packed with 25.3 g (30 ml) of a catalyst containing 2.2% of ruthenium and 3.4% of palladium on a magnesium oxide/aluminum oxide support (ratio MgO to $Al_2O_3$=10:90) in the form of 1 mm to 1.5 mm grit (prepared by filling the pores of an MgO/$Al_2O_3$ support with an aqueous ruthenium nitrate/palladium nitrate solution and drying at 120° C.). Reduction of the catalyst was effected by keeping it at a temperature of 220° C. for 7 hours under a stream of 60 standard liters of hydrogen per our under standard pressure after the temperature had been progressively raised from 100° to 220° C. over a period of 6 hours.

Through a tubular reactor (diameter 16 mm, packing height 15 cm, oil-heated double jacket), installed upstream of the hydrogenation reactor and packed with 20.3 g (29 ml) of γ-aluminum oxide in the form of 1.5 mm extrudates, there were pumped, per hour, 20.3 ml of 2-(2-cyanoethyl)-cyclohexanone (purity 98.2%. 20.3 g, 0.132 mole) and 600 ml of liquid ammonia (360 g, 21.2 moles) at a pressure of 230 bar and a temperature of 100° C., after which the mixture was passed downwardly through the hydrogenation reactor at a pressure of 210 bar and a temperature of 120° C. together with a stream of 60 standard liters (2.7 moles) of hydrogen per hour. Gas-chromatographic analysis revealed that the product mixture contained 69.5% of 2-(3-aminopropyl)-cyclohexylamine, 25.4% of decahydroquinoline, and 2.2% of 2-(3-aminopropyl)-cyclohexanol, corresponding to a yield of 2-(3-aminopropyl)-cyclohexylamine of 68.6% of theory.

Example 18

A vertical tubular reactor (diameter 16 mm, packing height 50 cm, oil-heated double jacket) was packed with 76.9 g (102 ml) of a catalyst containing 5% of ruthenium on a magnesium oxide/aluminum oxide support (30:70) in the form of 1 mm to 1.5 mm grit (prepared by filling the pores of a magnesium oxide/aluminum oxide support with an aqueous ruthenium nitrate solution and drying at 120° C.). Reduction of the catalyst was affected by keeping it at a temperature of 220° C. for 9 hours under a stream of 150 standard liters of hydrogen per our under a pressure of 100 bar after the temperature had been progressively raised from 100° to 220° C. over a period of 7 hours.

Through a tubular reactor (diameter 16 mm, packing height 50 cm, oil-heated double jacket), installed upstream of the hydrogenation reactor and packed with 67.2 g (96 ml) of γ-aluminum oxide in the form of 1.5 mm extrudates, there were pumped upwardly, per hour, 42.6 g of 2-(2-cyanoethyl)-cyclohexanone (purity 96%, 0.271 mole) and 1.283 ml of liquid ammonia (770 g, 45.3 moles) at a pressure of 250 bar and a temperature of 70° C. Hydrogen was then added to the stream at a rate of 90 standard liters (4.0 moles) per hour, and the effluent from the i-line imination reactor was passed upwardly through the hydrogenation reactor at a pressure of 250 bar and a temperature of 120° C. Gas-chromatographic analysis of the hydrogenation product obtained after an on-stream period of 18 hours indicated 541.9 g of 2-(3-aminopropyl)-cyclohexylamine. The yield of 2-(3-aminopropyl)-cyclohexylamine was 71.5% of theory.

Example 19

A vertical tubular reactor (diameter 16 mm, packing height 50 cm, oil-heated double jacket) was packed with 81.3 g (103 ml) of a catalyst containing 3% of ruthenium on a calcium oxide/aluminum oxide support (10:90) in the form of 1.5 mm extrudates (prepared by diffusion impregnation of a calcium oxide/aluminum oxide support with an aqueous ruthenium nitrate solution and drying at 100° C.). Reduction of the catalyst was effected by keeping it at a temperature of 220° C. for 9 hours under a stream of 150 standard liters of hydrogen per hour under a pressure of 100 bar after the temperature had ben progressively raised from 100° to 220° C. over a period of 7 hours.

Through a tubular reactor (diameter 16 mm, packing height 50 cm, oil-heated double jacket), installed upstream of the hydrogenation reactor and packed with 67.2 g (96 ml) of γ-aluminum oxide in the form of 1.5 mm extrudates, there were pumped upwardly, per hour, 37.1 g of 2-(2-cyanoethyl)-cyclohexanone (purity 96%, 0.236 mole) and 1,290 ml of liquid ammonia (774 g, 45.5 moles) at a pressure of 250 bar and a temperature of 70° C. Hydrogen was then added to the stream at a rate of 120 standard liters (5.4 moles) per hour, and the effluent form the in-line imination reactor was passed upwardly through the hydrogenation reactor at a pressure of 250 bar and a temperature of 120° C. Gas-chromatographic analysis of the hydrogenation product obtained after an on-stream period of 20.6 hours indicated 536.1 g of 2-(3-aminopropyl)-cyclohexylamine. The yield of 2-(3-aminopropyl)-cyclohexylamine was 70.5% of theory.

Example 20

A vertical tubular reactor (diameter 16 mm, packing height 50 cm, oil-heated double jacket) was packed with 90.1 g (87 ml) of a catalyst containing 3% of ruthenium on β-aluminum oxide in the form of 1.2 mm extrudates (prepared by filling the pores of β-aluminum oxide with an aqueous ruthenium nitrate solution and drying at 120° C.). Reduction of the catalyst was effected by keeping it at a temperature of 220° C. for 9 hours under a stream of 150 standard liters of hydrogen per hour, under a pressure of 100 bar, after the temperature had been progressively raised from 100° to 220° C. over a period of 7 hours.

Through a tubular reactor (diameter 16 mm, packing height 50 cm, oil-heated double jacket), installed upstream of the hydrogenation reactor and packed with 67.2 g (96 ml) of γ-aluminum oxide in the form of 1.5 mm extrudates, there were pumped upwardly, per hour, 22.6 g of 2-(2-cyanoethyl)-cyclohexanone (purity 96%, 0.144 mole) and 1,086 ml of liquid ammonia (652 g, 38.3 moles) at a pressure of 250 bar and a temperature of 70° C. Hydrogen was then added to the stream at a rate of 60 standard liters (2.7 moles) per hour, and the effluent from the in-line imination reactor was passed upwardly through the hydrogenation reactor at a pressure of 250 bar and a temperature of 120° C. Following separation and distillation of the product obtained after an on-stream period of 16.3 hours there were obtained, besides 43.5 g of decahydroquinoline, 291.7 g of 2-(3-aminopropyl)-cyclohexylamine. The yield of 2-(3-aminopropyl)-cyclohexylamine was 79.8% of theory.

Example 21

A vertical tubular reactor (diameter 16 mm, packing height 24 cm, oil-heated double jacket) was packed with 43.3 g (42 ml) of a catalyst containing 3% of ruthenium on β-aluminum oxide in the form of 1.2 mm extrudates (prepared by filling the pores of β-aluminum oxide with an aqueous ruthenium nitrate solution and drying at 120° C.). Reduction of the catalyst was effected by keeping it at a temperature of 220° C. for 9 hours under a stream of 150 standard liters of hydrogen per hour under a pressure of 100 bar after the temperature had been progressively raised from 100° to 220° C. over a period of 7 hours.

Through a tubular reactor (diameter 16 mm, packing height 50 cm, oil-heated double jacket), installed upstream of the hydrogenation reactor and packed with 67.2 g (96 ml) of γ-aluminum oxide in the form of 1.5 mm extrudates, there were pumped upwardly, per hour, 11.0 g of 2-(2-cyanoethyl)-cyclopentanone (purity 77.0%, 0.062 mole) and 535 ml of liquid ammonia (321 g, 18.9 moles) at a pressure of 250 bar and a temperature of 70° C. Hydrogen was then added to the stream at a rate of 60 standard liters (2.7 moles) per hour, and the effluent from the in-line imination reactor was passed upwardly through the hydrogenation reactor at a pressure of 250 bar and a temperature of 120° C. The product obtained after an on-stream period of 45.4 hours was worked up by fractional distillation. There were obtained 91.2 g of 1-azabicyclo[4.3.0]nonane (b.p.=80° C./50 mm Hg) and 224.4 g of 2-(3-aminopropyl)-cyclopentylamine (b.p.=122° C./28 mm Hg)l. The yield of 2-(3-aminopropyl)-cyclopentylamine was 56.3% of theory.

Comparative Example 1

37.8 g of 2-(2-cyanoethyl)-cyclohexanone (purity 98.2%), 25.5 ml of methanol and 3.8 g of Raney cobalt were placed in an autoclave having a capacity of 300 ml, which was purged with nitrogen before 60.0 g of liquid ammonia were pumped in. An internal hydrogen pressure of 110 bar was created and the mixture was heated to 130° C. with stirring. The hydrogen was replenished when the pressure dropped below 110 bar. Hydrogen absorption ceased after 5 hours. Ammonia and methanol were distilled off to yield a reaction mixture containing 22.1% of 2-(3-aminopropyl)-cyclohexylamine and 72.1% of decahydroquinoline, as determined by GCA. The yield of the diamine was 20.4%.

Comparative Example 2

A vertical tubular reactor (diameter 9 mm, oil-heated double jacket) was packed with 38.8 g (25 ml) of a commercial cobalt catalyst containing 5% of $Mn_3O_4$ in the form of 2 to 3 mm grit. Reduction of the catalyst was effected by keeping it at a temperature of 180° C. for 1 hour and at 200° C. for 15 hours under a stream of 25 standard liters of hydrogen per hour under a pressure of 60 bar after the temperature had been progressively raised from 110° to 180° C. over a period of 2 hours.

16 standard liters (0.7 mole) of hydrogen, 7 ml of 2-(2-cyanoethyl)-cyclohexanone (purity 98.2%, 6.9 g, 0.046 mole), and 37 ml (22 g, 1.3 mole) of liquid ammonia were passed, per hour, upwardly through the hydrogenation reactor at a temperature of 75° C. and a pressure of 98 bar and for an average residence time of 25.6 minutes. Gas-chromatographic analysis showed that the effluent contained 72% of decahydroquinoline, 4.1% of octahydroquinoline, 7.4% of 2-(3-aminopropyl)-cyclohexanol, and 13.1% of 2-(3-aminopropyl)-cyclohexylamine, corresponding to a yield of 2-(3-aminopropyl)-cyclohexylamine of 12.6% of theory.

Comparative Example 3

Comparative Example 2 was repeated at a temperature of 100° C. and a pressure of 98 bar, the average residence time being 4.9 minutes. 15 standard liters (0.7 mole) of hydrogen, 6.6 mol of 2-(2-cyanoethyl)-cyclohexanone (purity 98.2%, 6.5 g, 0.043 mole)m, and 216 ml (129 g, 7.6 moles) of liquid ammonia were passed, per hour, upwardly through the hydrogenation reactor. Gas-chromatographic analysis showed that the effluent contained 77.9% of decahydroquinoline, 2.0% of octahydroquinoline, 11.3% of 2-(3-aminopropyl)-cyclohexanol, and 6.0% of 2-(3-aminopropyl)-cyclohexylamine, corresponding to a yield of 2-(3-aminopropyl)-cyclohexylamine of 5.6% of theory.

Comparative Example 4

A vertical tubular reactor (diameter 9mm, oil-heated double jacket) was packed with 24.8 g (25 ml) of a catalyst containing 14.5% of cobalt on aluminum oxide in the form of 2 mm to 3 mm grit. Activation of the catalyst was effected by raising its temperature progressively from 100° to 300° C. over a period of 24 hours under a stream of 13 standard liters of hydrogen per hour and then keeping it at a temperature of 300° C. for 5 hours under a stream of 25 standard liters of hydrogen per hour, under standard pressure.

12 standard liters (0.5 mole) of hydrogen, 5.2 ml of 2-(2-cyanoethyl)-cyclohexanone (purity 98.2%, 5.1 g, 0.034 mole), and 172 ml (103 g, 6.1 moles) of liquid ammonia were passed, per hour, upwardly through the hydrogenation reactor at a temperature of 110° C. and a pressure of 98 bar and for an average residence time of 7.1 minutes. Gas-chromatographic analysis showed that the effluent contained 40.2% of decahydroquinoline, 21.2% of octahydroquinoline, 0.7% of 2-(3-aminopropyl)-cyclohexanol, and 34.2% of 2-(3-aminopropyl)-cyclohexylamine, corresponding to a yield of 2-(3-aminopropyl)-cyclohexylamine of 32.2% of theory.

Comparative Example 5

A vertical tubular reactor (diameter 14 mm, packing height 43 cm, oil-heated double jacket) was packed with 35.7 g (59.5 ml) of a catalyst containing 1.8% of ruthenium on aluminum oxide (manufactured by diffusion impregnation of aluminum oxide with an aqueous ruthenium chloride solution and drying at 70° C.). Reduction of the catalyst was effected by raising its temperature progressively from 100° to 220° C. over a period of 7 hours under a stream of 50 standard liters of hydrogen per hour and a pressure of 60 bar and then keeping it at a temperature of 220° C. for 5 hours under the same pressure.

60 standard liters (2.7 mole) of hydrogen, 16.1 ml of 2-(2-cyanoethyl)-cyclohexanone (purity 98.2%, 15.8 g, 0.104 mole), and 645 ml (387 g, 22.8 moles) of liquid ammonia were passed, per hour, upwardly through the hydrogenation reactor at a temperature of 90° C. and a pressure of 90 bar and for an average residence time of 4.0 minutes. Gas-chromatographic analysis showed that the effluent contained 44.9% of decahydroquinoline, 11.6% of octahydroquinoline, 6.5% of 2-(3-aminopropyl)-cyclohexanol, and 32.7% of 2-(3-aminopropyl)-cyclohexylamine, corresponding to a yield of 2-(3-aminopropyl)-cyclohexylamine of 31.0% of theory.

Comparative Example 6

Comparative Example 5 was repeated at a pressure of 200 bar. The effluent now contained 69.1% of decahydroquinoline, 18.3% of 2-(3-aminopropyl)-cyclohexanol, and 10.5% of 2-(3-aminopropyl)-cyclohexylamine, corresponding to a diamine yield of 9.9% of theory.

We claim:

1. A process for the preparation of a 2-(3-aminopropyl)-cycloalkylamine of the formula

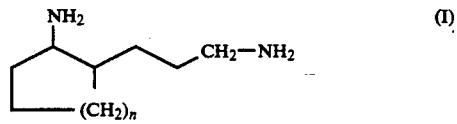
(I)

in which the subscript n is an integer from 1 to 4, from a 2-(2-cyanoethyl)-cycloalkanone of the formula

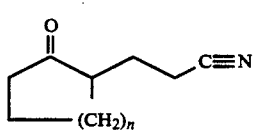

in which the subscript n has the meaning stated above, which process comprises carrying out the following stages in discrete reaction chambers:
 a) reacting the 2-(2-cyanoethyl)-cycloalkanone II in a first reaction chamber with excess ammonia over an acidic heterogeneous catalyst selected from the group consisting of aluminum oxide, silicon oxide, titanium dioxide, zirconium dioxide, aluminum phosphate and aluminosilicates at a temperature of from 20° to 150° C. and a pressure of from 15 to 500 bar, and
 b) in a second reaction chamber, the reaction product form stage a) is hydrogenated at a temperature of from 60° to 150° C. and a pressure of from 50 to 500 bar in the presence of excess ammonia over a hydrogenation catalyst containing at least one metal selected from the group consisting of cobalt, nickel, iron, copper and the noble metals of group VIII of the periodic table.

2. A process as claimed in claim 1, wherein the hydrogenation catalyst also includes as a basic component an oxide or hydroxide of an alkali metal or alkaline earth metal.

3. A process as claimed in claim 1, wherein the hydrogenation catalyst is support on a neutral or basic supporting material.

4. A process as claimed in claim 3, wherein the hydrogenation catalyst is supported on β-aluminum oxide or magnesium oxide/aluminum oxide.

5. A process as claimed in claim 1, wherein the hydrogenation catalyst is selected from the group consisting of cobalt and ruthenium on a basic supporting material.

6. A process as claimed in claim 1, wherein the acidic heterogeneous catalyst is selected from the group consisting of aluminum oxide, titanium dioxide, zirconium dioxide and silicon dioxide.

7. A process as claimed in claim 6, wherein the acidic heterogeneous catalyst is aluminum oxide.

8. A process as claimed in claim 6, wherein the acidic heterogeneous catalyst is titanium dioxide.

9. A process as claimed in claim 6, wherein the acidic heterogeneous catalyst is doped with a halide to raise its acidity.

10. A process as claimed in claim 9, wherein the catalyst is doped with a chloride.

11. A process as claimed in claim 1, wherein the process is carried out in the imination stage (a) with an overall residence time of about 0.5 to 120 minutes.

12. A process as claimed in claim 11, wherein said overall residence time is about 1 to 40 minutes.

13. A process as claimed in claim 11, wherein said overall residence time is about 1.5 to 20 minutes.

14. A process as claimed in claim 1, wherein the hydrogenation catalyst is ruthenium or ruthenium containing up to 5% by weight of palladium or iron.

15. A process as claimed in claim 1, wherein the hydrogenation catalyst is cobalt containing a basic component selected from the group consisting of alkali metal and alkaline earth metal oxides and hydroxides.

16. A process as claimed in claim 15, wherein the basic cobalt catalyst contains at least one additional element selected from the group consisting of iron, nickel, manganese, chromium, molybdenum, tungsten and phosphorus.

17. A process as claimed in claim 15, wherein the basic cobalt catalyst contains at least one additional metal selected from the group consisting of iron, nickel and manganese.

18. A process as claimed in claim 1, wherein the process is carried out continuously with a throughput of the reactant II of about 0.01 to 5 kg/kg/hr, using ammonia in an amount of about 5 to 500 moles per mole of the 2-(2-cyanoethyl)-cycloalkanone reactant II.

19. A process as claimed in claim 18, wherein the temperature for the catalytic hydrogenation is maintained at about 70° to 140° C. and the pressure is maintained at about 100 to 350 bar.

20. A process as claimed in claim 18, wherein the temperature for the catalytic hydrogenation is maintained at about 80° to 130° C. and the pressure is maintained at about 150 to 300 bar.

* * * * *

UNITED STATES PATENT AND TRADEMARK OFFICE
CERTIFICATE OF CORRECTION

PATENT NO. : 5,239,120

DATED : August 24, 1993

INVENTOR(S) : MERGER et al

It is certified that error appears in the above-identified patent and that said Letters Patent is hereby corrected as shown below:

Column 15:

Claim 1 b), line 2: change "form" to --from--.

Claim 3, line 2: change "support" to --supported--.

Signed and Sealed this

Fifth Day of April, 1994

Attest:

BRUCE LEHMAN

Attesting Officer

Commissioner of Patents and Trademarks